Oct. 24, 1950 H. C. SWIM Plant Pat. 983
ROSE PLANT
Filed Aug. 4, 1949
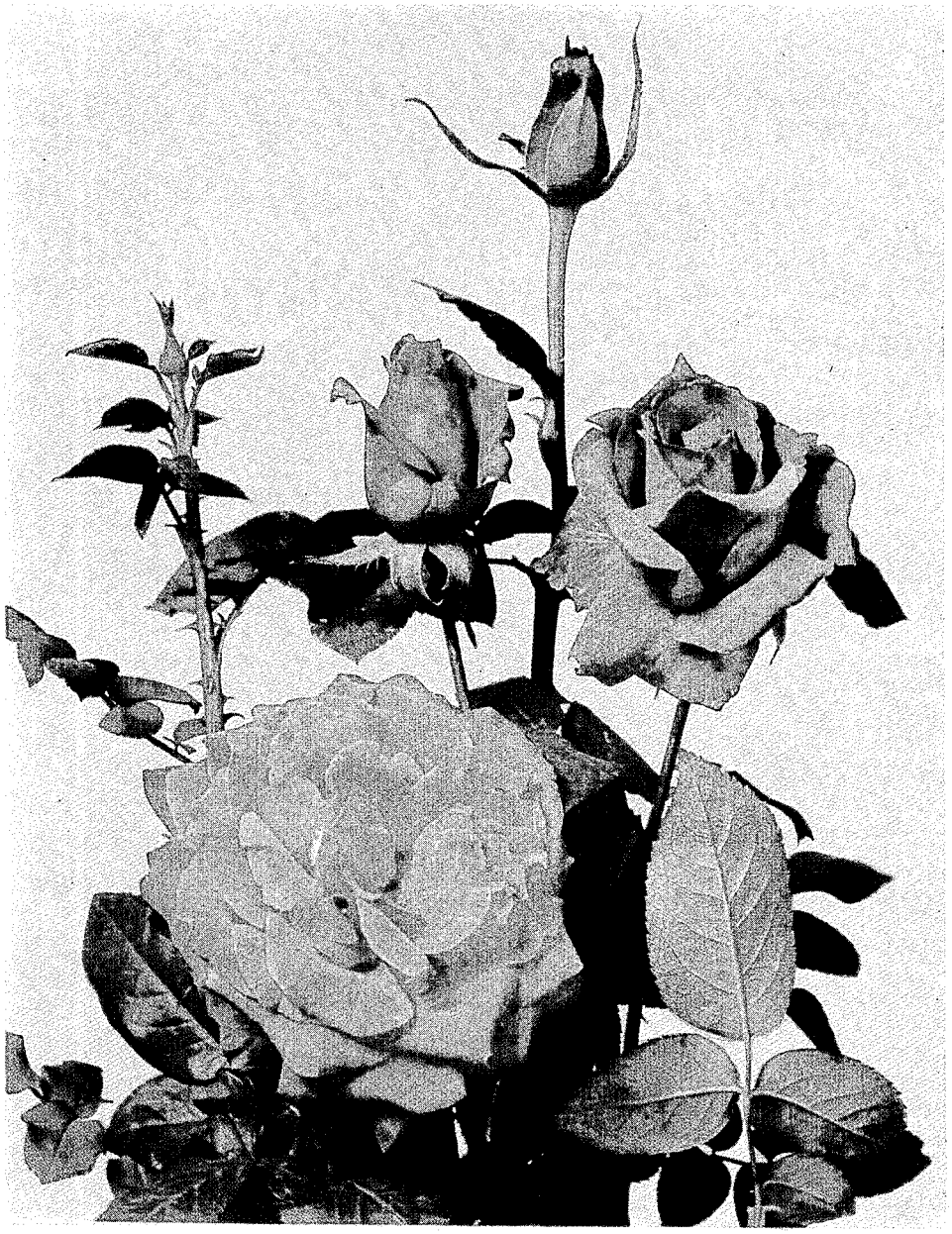
Inventor
H. C. Swim
By Robb & Robb
Attorneys Patented Oct. 24, 1950

Plant Pat. 983

UNITED STATES PATENT OFFICE

983

ROSE PLANT

Herbert C. Swim, Ontario, Calif., assignor to Armstrong Nurseries, Inc., Ontario, Calif., a corporation of California Application August 4, 1949, Serial No. 108,629

1 Claim. (Cl. 47—61)

The present invention relates to a new and distinct variety of rose plant resulting from crossing of two well known rose varieties, "World's Fair" and "Mirandy," the object of this cross being to improve upon certain characteristics of the parents more specifically referred to hereinafter.

This new variety is characterized as to novelty by exceptional brilliance in a shade of red that is unusual in roses of this dominant color, and the permanence of the red pigment throughout the life of each flower.

Other features of novelty reside in the form of the open flower, the petals of which are repand and form a wavy outline, bending slightly inwards and outwards in succession about their margins to an extent rarely found in other roses; the floriferousness of the variety which, combined with the large size of the flowers is exceptional; and the heavy substance of the petals which gives the flower lasting quality with respect to both form and color of the flower.

These characteristics, in combination, give to this new variety of rose qualities that make it distinct from any other rose known in commerce, so far as I am aware.

By way of comparison, this new variety is distinct from its seed parent in the following particulars:

(1) It is more upright in growth and the foliage is substantially larger than that of "World's Fair."

(2) The flowers are of larger size and more brilliant in color, as well as having a more substantial substance, giving them a better lasting quality both as to color and form of the flower.

(3) This new variety has a more greyed cast to the leaves than does "World's Fair."

The new variety is also distinct from its pollen parent in the following points:

(1) The flowers of this new variety are only slightly fragrant, whereas "Mirandy" flowers are intensely fragrant.

(2) The flower of this new variety is lighter and brighter in hue than the flower of "Mirandy" and tends to hold more constantly the color, which trait is in fact one of the outstanding characteristics of this new variety.

(3) This new variety characteristically produces many of its flowers in clusters, whereas the flowers of "Mirandy" are usually produced singly.

(4) This new variety has a flower that should be classed as double, whereas the flowers of "Mirandy" are classed as very double.

(5) The form of the flowers of this new variety is characterized by the repand shape of the petals which is not found in the pollen parent "Mirandy."

Asexual reproduction of this new variety shows the foregoing characteristics come true to form and are established.

In the drawings are shown specimens of the new variety at different stages of development of both the blossoms and the foliage.

This new variety was asexually reproduced at Ontario, California, by budding.

The following is a detailed description of the new variety, all reference to color being in accordance with the Robert F. Wilson Horticultural Colour Chart, 1938, except where indicated to be in accordance with Ridgway's Color Standards and Nomenclature:

Type: Bush; outdoor; seedling; for cut flowers and garden decoration.

Class: Hybrid polyantha tea.

Breeding: Seedling.

*Seed parent.*—"World's Fair" (Pl. Pat. No. 362).

*Pollen parent.*—"Mirandy" (Pl. Pat. No. 632). 632).

Propagation: Holds its distinguishing characteristics through succeeding propagations.

*Flower*

Locality where grown: Ontario, California.

Flowers borne: Sometimes singly, usually two to five or more to stem; in irregular cluster; on normal strength, short to medium length stems.

Quantity of bloom: Very free; outdoors.

Continuity: Intermittent but nearly continuous during growing season.

Fragrance: Slight; tea to spicy.

Bud:

*Peduncle.*—Average length; average caliper; erect; usually rough due to some stiff gland-tipped cilia. Color — Absinthe Green, Plate XXXI (Ridgway), shaded lightly with Vandyke Red, Plate XIII (Ridgway), especially at cilia bases.

*Before calyx breaks.* — Size — medium. Form—medium length; pointed to ovoid with foliaceous appendages, with foliaceous parts extending beyond the tip of the bud equal to one-fourth or more of its length.

*As calyx breaks.*—Color—Oxblood Red, Plate 00823, page 191.

*Sepals.*—Inner surface with tomentum; margins that are covered have tomentum, while uncovered margins have stipitate glands.

*As first petal opens.*—Size—average. Form—medium length; pointed to ovoid. Color—outside—near Cardinal Red, Plate 822/1, page 168; inside—near Currant Red, Plate 821/1, page 167, with shadings of Cardinal Red, Plate 822/1, page 168, and an iridescent sheen.

*Opening.*—Opens up well. Is not retarded from opening by cold, hot or dry weather.

Bloom: Size, when fully open—large; 4 inches to 4¾ inches.

*Petalage.*—Double; from 36 to 46 petals; plus 3 to 12 petaloids; arranged regularly.

*Form.*—Urn shaped at first; becoming flat to cupped; petals at first with tips reflexed; becoming later at maturity somewhat loosely rolled outward.

Petals:

*Texture.*—Moderately leathery; with inside velvety and outside slightly satiny.

*Shape.*—Outside—nearly oval to broadly obovate. Intermediate—broadly obovate with apex rounded. Inside—broadly obovate; repand.

*Color.*—Colors may be modified by being overlaid, shaded and/or tinted with other colors.

This description of a newly opened flower was made from a rose grown outdoors in the month of October, at Ontario, California:

*Color.*—*Outside petal*—outside surface: Cardinal Red, Plate 822/2, page 168, with shadings of Chrysanthemum Crimson, Plate 824/1, page 169; inside surface: Cardinal Red, Plate 822/3, page 168, near base, with rest of petal near Cardinal Red, Plate 822/1, page 168, somewhat iridescent. *Intermediate petal*—outside surface: Cardinal Red, Plate 822/2, page 168; inside surface: Currant Red, Plate 821/2, page 167, with iridescent sheen. *Inner petal*—outside surface: Cardinal Red, Plate 822/3, page 168; inside surface: near Currant Red, Plate 821/2, page 167, with iridescent sheen.

This description was made from a rose that was open for three days outdoors in the month of September, at Ontario, California.

*Color.*—*Outside petal*—outside surface: between Cardinal Red, Plate 822/2, page 168, and Chrysanthemum Crimson, Plate 824/2, page 169; inside surface: near Cardinal Red, Plate 822/1, page 168, with iridescent sheen. *Inside petal*—outside surface: between Cardinal Red, Plate 822/2, page 168, and Chrysanthemum Crimson, Plate 824/2, page 169; inside surface: near Cardinal Red, Plate 822/1, page 168, with pencillings of Indian Lake, Plate 826/1, page 170, toward petal margins, with iridescent sheen.

*General color effect.*—Newly opened flower—Currant Red, Plate 821/2, page 167, with an iridescent sheen. Three days open—between Chrysanthemum Crimson, Plate 824/2, page 169, and Cardinal Red, Plate 822/2, page 168.

*Behavior.*—Drop off cleanly except for petaloids; fading very slightly—remaining near Chrysanthemum Crimson, Plate 824/2, page 169, until dry; not affected by hot or dry weather.

*Flower longevity.*—On bush in garden—5 to 6 days in October. Cut roses grown outdoors kept at living-room temperatures—3 to 4 days in October.

*Reproductive organs*

Stamens: Few; arranged irregularly about pistils; a few mixed with petaloids.

Filaments: Short to medium length; 7–12 mm.; most with anthers. Color—Camellia Rose, Plate 622, page 148.

Anthers: Color—Central portions—Amber Yellow, Plate 505/3, page 132. Outer portions—near Cadmium Orange, Plate 8/1, page 8.

Pollen: Moderate. Color — Cadmium Orange, Plate 8/1, page 8.

Pistils: Very many; approximately 140 in number.

Styles: Moderately even; average length; average caliper; loosely bunched. Color — Carmine Rose, Plate 621, page 75.

Stigma: Color—Chrome Yellow, Plate 605/2, page 144, with a translucent effect.

Ovaries: Usually all enclosed in calyx.

Hips: Average size; pyriform; smooth; walls thin, fleshy. Color—three-fourths mature hip—between Lime Green, Plate XXXI (Ridgway) and Chrysolite Green, Palte XXXI (Ridgway).

Sepals (from fully open flowers): Permanent; long; spear-shaped; reflexed. Color—inside—between Corydalis Green, Plate XLI (Ridgway), and Light Grape Green, Plate XLI (Ridgway), slightly tinted with Dark Vinaceous, Plate XXVII (Ridgway); outside—Biscay Green, Plate XVII (Ridgway).

Seeds: Average number; medium size; 8 to 14 in number.

*Plant*

Foliage:

*Leaves.*—Compound of usually five leaflets; normal amount; medium size to large; moderately heavy; glaucous.

*Leaflets.*—Shape—ovate with apex narrowly acute; base round to obtuse to shallowly cordate; margin usually doubly serrate. Color — Mature — upper surface: Sage Green, Plate 000861, page 198; under surface: between Light Grape Green, Plate XLI (Ridgway) and Asphodel Green, Plate XLI (Ridgway). Young—upper surface: Light Cress Green, Plate XXXI (Ridgway) overlaid with Indian Red, Plate XXVII (Ridgway); under surface: Light Grape Green, Plate XLI (Ridgway) overlaid with Indian Red, Plate XXVII (Ridgway).

*Rachis.*—Average size. Upper side—grooved with some stipitate glands on edges. Under side—moderately prickly.

*Stipules.*—Medium length (11 mm.); medium width with short to medium length points, turning out at an angle of more than 45°, recurved toward the stem.

*Disease.*—More than average resistance to mildew.

Growth:

*Habit.*—Bushy; upright-spreading; moderately branched.

*Growth.*—Moderate.

*Canes.*—Medium caliper.

*Main stems.*—Color—near Rainette Green, Plate XXXI (Ridgway). *Large prickles*—several to many; moderately short, hooked slightly downward; with short narrow base. Color—near Sayal Brown, Plate XXIX (Ridgway). *Small prickles*—several. Color—near Sayal Brown, Plate XXIX (Ridgway). *Hairs*—none.

*Branches.*—Color—between Asphodel Green, Plate XLI (Ridgway) and Light Grape Green, Plate XLI (Ridgway). *Large prickles*—several; moderately short, almost straight, hooked slightly downward; with short very narrow base. Color—Straw Yellow, Plate XVI (Ridgway). *Small prickles*—many. Color—Reed Yellow, Plate XXX (Ridgway). *Hairs*—none but with many stipitate glands. Color—Reed Yellow, Plate XXX (Ridgway).

*New shoots.*—Color—between Rainette Green, Plate XXXI (Ridgway) and Light Cress Green, Plate XXXI (Ridgway), somewhat overlaid with Indian Red, Plate XXVII (Ridgway). *Large prickles*—several; medium length, hooked slightly downward; with medium length narrow base. Color—near Kildare Green, Plate XXXI (Ridgway), tinted with Acajou Red, Plate XIII (Ridgway). *Small prickles*—several. Color—near Kildare Green, Plate XXXI (Ridgway), tinted with Acajou Red, Plate XIII (Ridgway). *Hairs*—none, but with stipitate glands.

I claim:

A new and distinct variety of rose plant characterized as to novelty by the color of its blossoms and the permanence of the red pigment throughout the life of said blossoms; by the repand form of the flower petals; by the floriferousness of the variety combined with the large size of the flowers; and by the substance of the petals which gives the flower lasting quality both with respect to its form and its color, substantially as shown and described.

HERBERT C. SWIM,

No references cited.